(12) United States Patent
Hesch et al.

(10) Patent No.: US 8,548,740 B2
(45) Date of Patent: Oct. 1, 2013

(54) SYSTEM AND METHOD FOR WAVELET-BASED GAIT CLASSIFICATION

(75) Inventors: Joel Hesch, Minneapolis, MN (US); Yunqian Ma, Plymouth, MN (US); Peter Lommel, St. Cloud, MA (US)

(73) Assignee: Honeywell International Inc., Morristown, NJ (US)

( * ) Notice: Subject to any disclaimer, the term of this patent is extended or adjusted under 35 U.S.C. 154(b) by 476 days.

(21) Appl. No.: 12/900,315

(22) Filed: Oct. 7, 2010

(65) Prior Publication Data

US 2012/0089330 A1 Apr. 12, 2012

(51) Int. Cl.
*G01C 21/00* (2006.01)
(52) U.S. Cl.
USPC ............................................ 701/479
(58) Field of Classification Search
None
See application file for complete search history.

(56) References Cited

U.S. PATENT DOCUMENTS

| | | | |
|---|---|---|---|
| 5,349,441 A | 9/1994 | Sanders | |
| 5,583,776 A | 12/1996 | Levi et al. | |
| 6,522,266 B1 | 2/2003 | Soehren et al. | |
| 6,546,336 B1 | 4/2003 | Matsuoka et al. | |
| 6,571,193 B1 | 5/2003 | Unuma et al. | |
| 6,813,582 B2 | 11/2004 | Levi et al. | |
| 6,882,955 B1 | 4/2005 | Ohlenbusch et al. | |
| 6,981,019 B1 * | 12/2005 | Boies et al. | 709/204 |
| 7,526,402 B2 | 4/2009 | Tanenhaus et al. | |
| 7,561,960 B2 | 7/2009 | Soehren | |
| 7,647,196 B2 | 1/2010 | Kahn et al. | |
| 7,653,508 B1 | 1/2010 | Kahn et al. | |
| 2001/0022828 A1 | 9/2001 | Pyles | |
| 2005/0033200 A1 | 2/2005 | Soehren et al. | |
| 2005/0197769 A1 | 9/2005 | Soehren et al. | |
| 2009/0161915 A1 | 6/2009 | Chen et al. | |
| 2011/0153043 A1 * | 6/2011 | Ojala | 700/94 |
| 2012/0069131 A1 * | 3/2012 | Abelow | 348/14.01 |

FOREIGN PATENT DOCUMENTS

| | | |
|---|---|---|
| EP | 1253404 | 10/2002 |
| EP | 1906146 | 4/2008 |
| WO | 2005091113 | 9/2005 |
| WO | 2009023923 | 2/2009 |

OTHER PUBLICATIONS

European Patent Office, "European Search Report", "From EP counter part", mailed Jan. 20, 2012, Published in: EP.
European Patent Office, "European Search Report", mailed Jan. 31, 2012, pp. 13, Published in: EP.
Bors, "Introduction of the Radial Basis Function (RBF) Networks", 2000, Publisher: Online Symposium for Electronics Enginners.

(Continued)

*Primary Examiner* — Thomas Tarcza
*Assistant Examiner* — Adam Alharbi
(74) *Attorney, Agent, or Firm* — Fogg & Powers LLC (57) ABSTRACT

A motion classification system comprises an inertial measurement unit configured to sense motion of a user and to output one or more channels of inertial motion data corresponding to the sensed motion; and a processing unit configured to calculate a coefficient vector for each of the one or more channels based on a wavelet transformation of the respective inertial motion data, and to select one of a plurality of gaits as the user's gait based on the calculated coefficient vector of at least one of the one or more channels and on a plurality of templates, each template corresponding to one of the plurality of gaits.

20 Claims, 6 Drawing Sheets

(56) References Cited

OTHER PUBLICATIONS

Buhmann, M.D., "Radial Basis Functions: Theory and Implementations", 2000, "Acta Numerica" Publisher: The University of Cambridge, Published in: United Kingdom, p. 1-38.

Chau, "A Review of Analytical Techniques for Gait Data. Part 2: Neutral Network and Wavelet Methods", "Gait and Posture", May 7, 2000, pp. 102-120, vol. 13.

Grejner-Brzezinska et al. "Multi-Sensor Personal Navigator Supported by Human Motion Dynamics Model", "3rd IAG/12th FIG Symposium", May 22-24, 2006.

Hanson et al., "Neutral Network Gait Classification for On-Body Inertial Sensors", "Sixth International Workshop on Wearable and Implantable Body Sensor Networks, 2009", Jun. 3-5, 2009, pp. 181-186, Publisher: IEEE, Published in: Berkeley, CA.

Lau et al., "Support Vector Machine for Classification of Walking Conditions Using Miniature Kinematic Sensors", Mar. 18, 2008, pp. 563-573, vol. 46, Publisher: International Federation for Medical and Biological Engineering 2008.

Morris et al., "A Compact Wearable Sensor Package for Clinical Gait Monitoring", "Offspring, http://www.media.mit.edu/Motorola/Offspring/", Jan. 31, 2003, pp. 7-15, vol. 1, No. 1.

Rahati et al., "Gait Recognition Using Wavelet Transform", "Fifth International Conference on Information Technology: New Gererations, 2008", Apr. 7-9, 2008, pp. 932-936, Publisher: IEEE, Published in: Las Vegas, NV.

Rong et al., "A Wearable Acceleration Sensor System for Gait Recognition", "2nd IEEE Conference on Industrial Electronics and Applications, 2007", May 23-25, 2007, Publisher: IEEE.

Sabatini, "Quaternion-Based Strap-Down Integration Method for Applications of Inertial Sensing to Gait Analysis", "Medical & Biological Engineering & Computing 2005", Jul. 19, 2004, pp. 94-101, vol. 53.

Sahin, "A Radical Basis Function Approach to a Color Image Classification Problem in a Real Time Industrial Application; Chapter 3 Radical Basis Function Networks", Jun. 27, 1997, Publisher: Virginia Tech.

Sevnsson et al., "Stair Gait Classification From Kinematic Sensors", Aug. 2007.

Soehren, Wayne and Wes Hawkinson, "Prototype Personal Navigation System", "IEEE A&E Systems Magazine; Based on Presentation at PLANS 2006", Apr. 2008, Publisher: IEEE.

European Patent Office, "Office Action", Feb. 27, 2012, Published in: EP.

* cited by examiner

SYSTEM AND METHOD FOR WAVELET-BASED GAIT CLASSIFICATION

BACKGROUND

Personal navigation systems have received attention from both the industrial and academic research communities in recent years. Numerous target applications have been proposed, including localization for members of a team of firefighters, first responders, and soldiers. In these applications, the safety and efficiency of the entire team depends on the availability of accurate position and orientation (pose) estimates of each team member. While the team is operating within the coverage area of GPS satellites, each person's pose can be reliably estimated. However, a far more challenging scenario occurs when the team is inside a building, in an urban canyon, or under a forest canopy. In these cases, GPS-based global localization is not sufficiently accurate or may be completely unavailable, and pose estimation must be accomplished through secondary means. One popular approach is to equip each person with a body-mounted strap-down Inertial Measurement Unit (IMU) typically comprising three accelerometers and three gyroscopes in orthogonal triads, which measure the person's motion. To mitigate the drift errors in strap-down inertial navigation, conventional systems typically include aiding sensors, such as a camera or laser scanner which sense the color, texture, or geometry of the environment. Each person's pose can then be estimated individually by fusing the available sensing information.

SUMMARY

In one embodiment, a motion classification system is provided. The motion classification system comprises an inertial measurement unit configured to sense motion of a user and to output one or more channels of inertial motion data corresponding to the sensed motion; and a processing unit configured to calculate a coefficient vector for each of the one or more channels based on a wavelet transformation of the respective inertial motion data, and to select one of a plurality of gaits as the user's gait based on the calculated coefficient vector of at least one of the one or more channels and on a plurality of templates, each template corresponding to one of the plurality of gaits.

DRAWINGS

Understanding that the drawings depict only exemplary embodiments and are not therefore to be considered limiting in scope, the exemplary embodiments will be described with additional specificity and detail through the use of the accompanying drawings, in which.

In accordance with common practice, the various described features are not drawn to scale but are drawn to emphasize specific features relevant to the exemplary embodiments.

DETAILED DESCRIPTION

In the following detailed description, reference is made to the accompanying drawings that form a part hereof, and in which is shown by way of illustration specific illustrative embodiments. However, it is to be understood that other embodiments may be utilized and that logical, mechanical, and electrical changes may be made. Furthermore, the method presented in the drawing figures and the specification is not to be construed as limiting the order in which the individual acts may be performed. The following detailed description is, therefore, not to be taken in a limiting sense.

Figure 1:
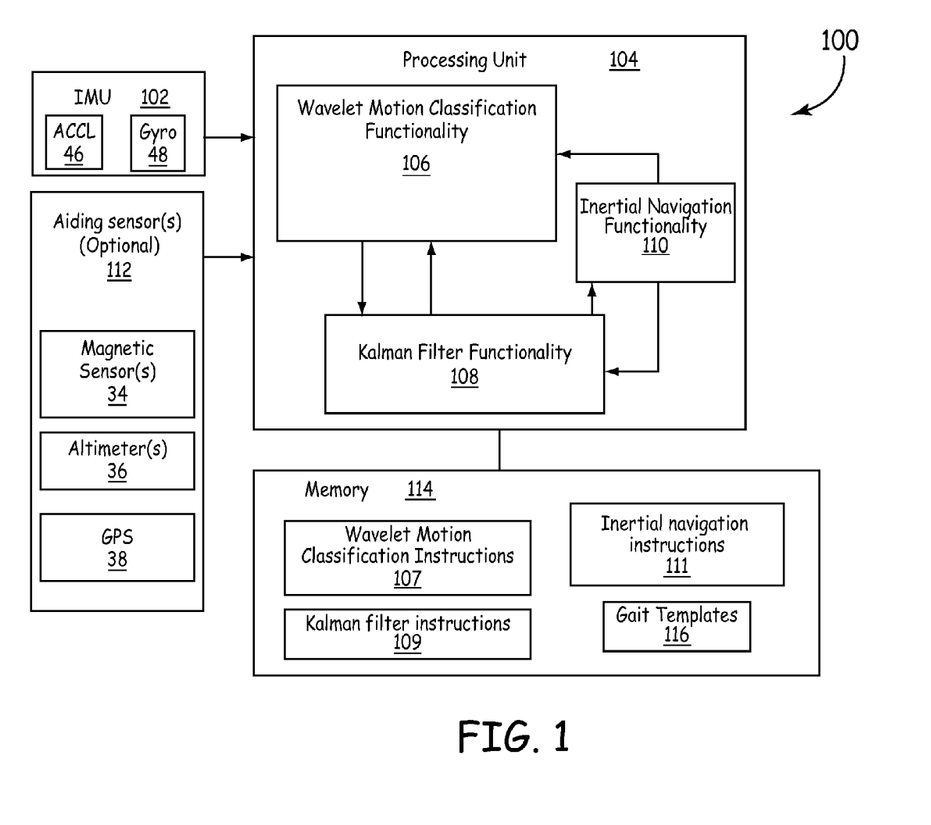
FIG. 1 is a block diagram depicting one embodiment of a personal navigation system.

FIG. 1 is a block diagram of one embodiment of a personal navigation system 100 worn by a user. System 100 includes an IMU 102 configured to provide data regarding the motion of the user wearing the personal navigation system 100. For example, in this embodiment, the IMU 102 includes three mutually orthogonal linear accelerometers and three mutually orthogonal gyroscopes to provide six channels of data. The IMU 102 provides the inertial motion data to a processing unit 104. In some embodiments of the personal navigation system 100, the IMU is implemented as a Microelectromechanical system (MEMS) based inertial measurement unit, such as a Honeywell BG1930 MEMS inertial measurement unit.

The processing unit 104 implements wavelet motion classification functionality 106, Kalman filter functionality 108, and inertial navigation functionality 110. The inertial navigation functionality 110 calculates a navigation solution including heading, speed, position, etc., based on the inertial motion data received from the IMU 102 using techniques known to one of skill in the art.

The wavelet motion classification functionality 106 performs a wavelet transform on at least one of the six channels of inertial motion data from the IMU 102 to obtain at least one wavelet transform. The wavelet motion classification functionality 106 then compares the wavelet transforms to a plurality of gait templates 116 stored in memory 114. The wavelet motion classification functionality 106 identifies the template which most closely matches the at least one wavelet obtained from the received inertial motion data based on a statistical analysis. Each gait template 116 corresponds to a particular user gait, frequency, and phase. As used herein, the terms "gait" and "gait mode" refer to the pattern of movement of the user's limbs while moving from one location to another. Thus, each gait mode is comprised of a pattern of repetitive motions. Exemplary gait modes include, but are not limited to, level walking, stair ascending/descending, sideshuffle walking, duck (firefighter) walking, hand-and-knee crawling, military (elbow) crawling, jogging, running, and sprinting. In addition, in some embodiments, a "no-model" hypothesis is stored in memory 114. The "no-model" hypothesis is a default hypothesis that covers the instances when the executed motion, as represented by the wavelet, does not match any of the stored gait templates 116.

The terms "frequency" and "gait frequency" refer to how quickly the corresponding motion is repeated. For example, the frequency of level walking refers to how quickly each step is repeated. The terms "phase" and "gait phase" refer to the shift in the starting position of the repetitive motion. For example, measurement of a step in the level walking gait mode can be started while one of the user's feet is passing the other (i.e., during swing phase), or with one foot in front of the other, etc.

After identifying the user's gait mode, the wavelet motion classification functionality 106 calculates a distance-traveled estimate based on the identified type of motion or gait mode.

Additional details regarding operation of the wavelet motion classification functionality 106 are described below. The distance-traveled estimate is output to the Kalman filter functionality 108.

In some embodiments, the system 100 also includes one or more aiding sensors 112 which provide additional motion data to the Kalman filter functionality 108. The Kalman filter functionality 108 calculates corrections to the navigation solution based on the distance-traveled estimate received from the wavelet motion classification functionality 106 and, optionally, on motion data received from the aiding sensors 112 if available, as described in more detail below. In the exemplary embodiment shown in FIG. 1, the optional aiding sensors 112 include one or more magnetic sensors 34, one or more pressure sensors or altimeters 36, and one or more global positioning satellite (GPS) receivers 38.

The corrections from the Kalman filter functionality 108 are provided to the inertial navigation functionality 110. In addition, in some embodiments, corrections to the distance-traveled estimate are provided from the Kalman filter functionality 108 to the wavelet motion classification functionality 106.

The processing unit 104 includes or functions with software programs, firmware or other computer readable instructions for carrying out various methods, process tasks, calculations, and control functions, used in the implementing the functionality described above.

These instructions are typically stored on any appropriate computer readable medium used for storage of computer readable instructions or data structures. The computer readable medium can be implemented as any available media that can be accessed by a general purpose or special purpose computer or processor, or any programmable logic device. Suitable processor-readable media may include storage or memory media such as magnetic or optical media. For example, storage or memory media may include conventional hard disks, Compact Disk—Read Only Memory (CD-ROM), volatile or non-volatile media such as Random Access Memory (RAM) (including, but not limited to, Synchronous Dynamic Random Access Memory (SDRAM), Double Data Rate (DDR) RAM, RAMBUS Dynamic RAM (RDRAM), Static RAM (SRAM), etc.), Read Only Memory (ROM), Electrically Erasable Programmable ROM (EEPROM), and flash memory, etc. Suitable processor-readable media may also include transmission media such as electrical, electromagnetic, or digital signals, conveyed via a communication medium such as a network and/or a wireless link.

In the exemplary embodiment shown in FIG. 1, the processing unit 104 executes inertial navigation instructions 111 stored on a memory 114 in implementing the inertial navigation functionality 110. Similarly, the processing unit 104 executes wavelet motion classification instructions 107 and Kalman filter instructions 109, also stored on memory 114 in this example, in implementing the wavelet motion classification functionality 106 and the Kalman filter functionality 108, respectively.

The Kalman filter functionality 108 outputs Kalman filter corrections as discussed above. In one implementation, the Kalman filter functionality 108 also pre-processes and/or pre-filters the input to the Kalman filter prior to calculating the corrections. As described above, the wavelet motion classification functionality 106 identifies the gait of the user to which the personal navigation system 100 is strapped. The gait is identified based on the received inertial data from the IMU 102. In particular, the wavelet motion classification functionality 106 performs a wavelet transform on each of the six channels of the received inertial motion data from the IMU 102 in this example.

Prior to performing the wavelet transform on a channel, the wavelet motion classification functionality 106 optionally partitions or segments the channel data into one cycle of the repetitive motion. In particular, during a training phase or mode, described in more detail below, the channel data is partitioned. However, during an identification phase or mode, explained in more detail below, the channel data is optionally partitioned. For example, the channel data can be partitioned intermittently if verification of the detected frequency is desired.

Figure 2:
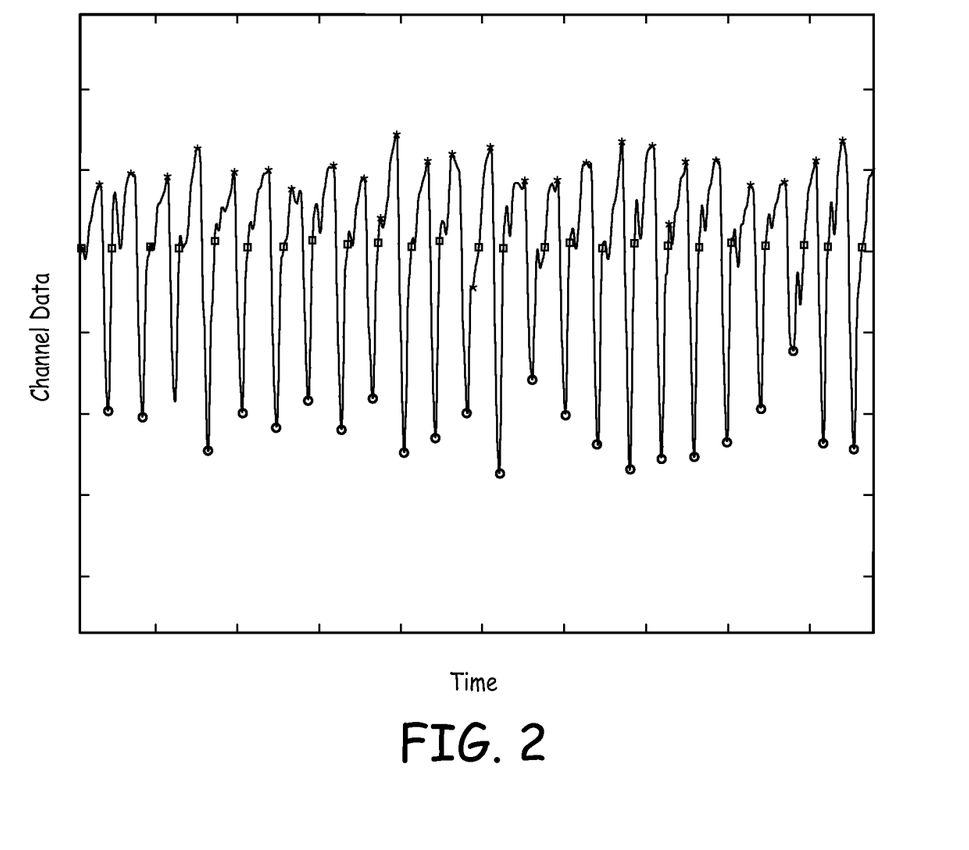
FIG. 2 is an exemplary diagram of a single channel of inertial motion data.

The channel data is segmented to represent a single step for gait modes related to walking or running For purposes of explanation, the cycle of repetitive motion is generally referred to herein as a "step" although it may refer to motions of parts of the body other than the legs, such as the arms or torso in a military crawl. The channel data can be segmented based on one or more of a plurality of techniques, such as peak detection, valley detection, or zero crossing. For example, FIG. 2 represents exemplary data for a single channel. A single step can be identified by segmenting the data from peak to peak, where the peaks are represented by an asterisk (*). Alternatively, the step can be identified by segmenting the data from valley to valley, where a valley is represented by an open circle (0). Additionally, the step can be segmented from zero crossing to zero crossing, where the zero crossing is represented as an open square (□) in FIG. 2.

As can be ascertained from FIG. 2, the technique used to segment the inertial motion data depends on the IMU signal. For example, in the exemplary data shown in FIG. 2, segmenting the steps based on valleys rather than peaks yields more accurate results. This is due to the many false peaks in the signal which are not the desired peaks for segmenting the steps.

In addition, in some embodiments an average step for a channel is calculated based on the segmented steps for the respective channel. For example, the data in FIG. 2 can be segmented into a plurality of steps using one of the techniques discussed above. The multiple segmented steps are then combined to form a single average step. After calculating the average step or selecting a representative actual step from the data, the wavelet motion classification functionality 106 then performs a wavelet transform on the step data.

Figure 3:
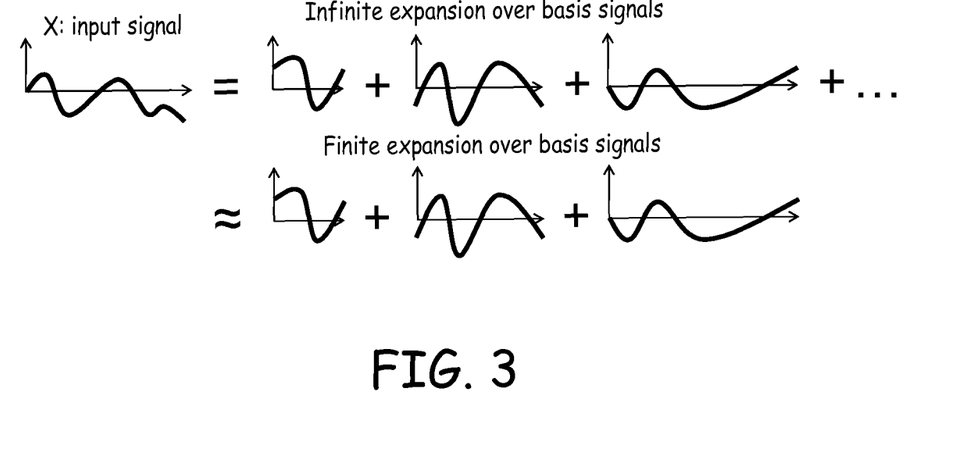
FIG. 3 is an exemplary diagram of a wavelet transform.

An exemplary wavelet transform is represented in FIG. 3. As shown in FIG. 3, a wavelet transform involves approximating the input signal (which represents a step in the channel data) as a finite expansion over basis signals using techniques known to one of skill in the art. The finite expansion is an approximation of the infinite expansion of the input signal. The finite expansion can be expressed mathematically by the following equation:

$$c_1\Phi + c_2\Phi + c_3\Phi$$

In the above equation, c1, c2, and c3 are expansion coefficients that define the finite expansion for a given channel. Thus, the signal approximated by the finite expansion can be represented by a coefficient vector containing the expansion coefficients. By comparing the coefficient vectors of each of the plurality of channels representing a step in the measured inertial motion data to corresponding coefficient vectors of known gait templates, the wavelet motion classification functionality 106 is able to identify the gait of the measured step. That is, based on a statistical analysis, the gait template which most closely matches the coefficient vectors is identified as the gait of the measured step.

It is to be understood that the data in FIGS. 2 and 3 is provided by way of example. In particular, actual data will depend, for example, on the particular user, the gait mode, gait frequency, gait phase, and channel of inertial motion data.

Figure 4:
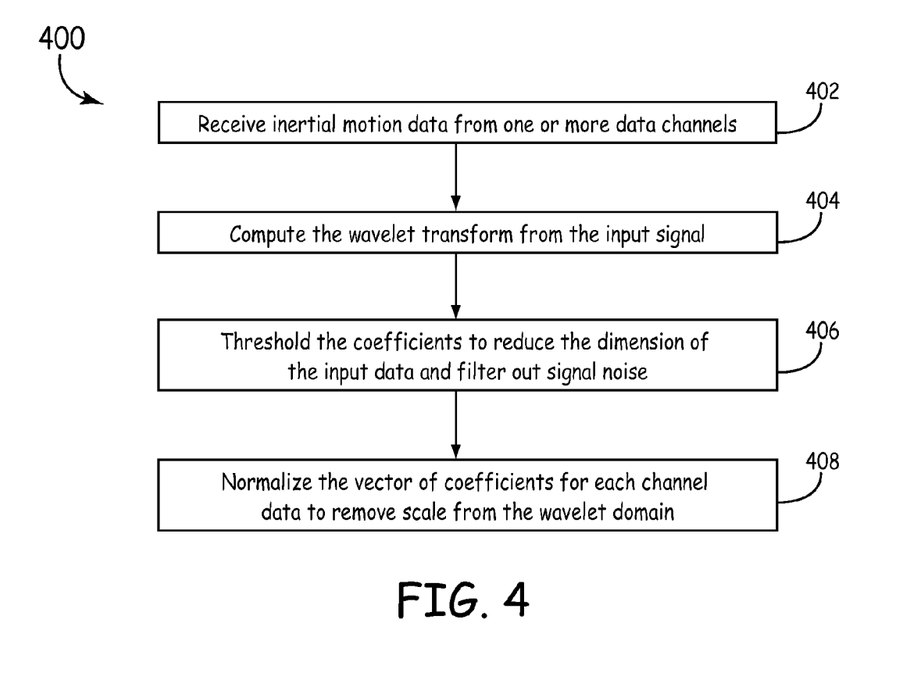
FIG. 4 is flow chart depicting one embodiment of a method for computing and storing the wavelet coefficient vectors.

One embodiment of a wavelet transform method 400 is shown in FIG. 4. In one instantiation of the wavelet transformation method 400, input from one of the up to six input channels of IMU data is received at block 402. Using techniques known to one of skill in the art, a full wavelet transformation is computed at block 404 using one of a selected wavelet type (e.g., Haar, Daubechies, etc.). At block 406, noise is removed and the dimensionality of the data is decreased by keeping only a selected number, N, of the largest coefficients. At block 408, in order to normalize for the effect of scale between IMU data channels, each wavelet coefficient vector is converted into a unit-length vector with the same direction.

Returning to FIG. 1, in some embodiments, the gait templates 116 are loaded onto the memory 114 based on previous empirical studies. In other embodiments, the wavelet motion classification functionality 106 is configured to operate in a training mode to generate the gait templates 116. Thus, in some embodiments, the wavelet motion classification functionality 106 is configured with two modes of operation: a training mode and an identification mode. The training mode is used to generate the gait templates 116 based on samples of one or more known gaits. An exemplary method of generating the gait templates in the training mode is described in more detail below with respect to FIG. 4. The identification mode is used to match a sample of an unknown gait to one of the gait templates 116 as described above. An exemplary method of identifying a user's gait in the identification mode is described in more detail below with respect to FIG. 5.

After identifying the gait mode of an unknown step, the wavelet motion classification functionality 106 is able to calculate a distance-traveled estimate. In particular, each gait template 116 is associated with a particular gait, frequency, and phase. Thus, by matching the unknown step to a gait template 116, the associated data for each gait template can be used to calculate the distance-traveled estimate. In some embodiments, the distance-traveled estimate is provided to the Kalman filter functionality 108 as a measurement update for the displacement between two consecutive positions: the person's position at the start of the step, and the person's position at the end of the step. In this instance, the distance-traveled estimate is first validated using a chi-squared residual test to ensure that spurious measurements are not processed by the Kalman filter functionality 108. It is to be understood that other techniques can be used in other embodiments, to calculate the distance-traveled estimate based on the identified gait mode. In addition, in other embodiments, the distance-traveled estimate can be input into the Kalman filter functionality 108 to be used in calculating corrections to other states in the navigation solution (e.g., instantaneous velocity). However, if the unknown step belongs to the no-model hypothesis discussed above, then no distance-traveled estimate is transmitted to the Kalman filter functionality 108 in some implementations.

As discussed above, the system 100 also optionally includes one or more aiding sensors 112. Data from the aiding sensors 112 is also input to the Kalman filter for use in calculating corrections to the navigation solution. For example, the magnetic sensors 34 are available to initialize the heading estimate as well as to provide heading information for the personal navigation system 100 during operation. In one example, the data from the magnetic sensors 34 is used to determine the person's direction of travel. For example, in some embodiments, the magnetic sensors 34 consist of three magnetic sensors mounted orthogonally. The processing unit 104 calculates a distance-traveled estimate and direction of travel based on the frequency of step available from the wavelet motion classification functionality 106, along with the heading of the steps as measured by the magnetic sensors 34.

In this example, the altimeters 36 infer additional information about the user's state. In this case, barometric altimeter altitude measurements are processed by the processing unit 104 to measure the user's elevation. The sequence of elevation measurements is correlated with a database of terrain elevation maps to form position error estimates. Position drift distorts the relative spacing between elevation measurements. The processing unit 104 predicts terrain correlation position to fix the accuracy of the location. The terrain correlation is predicted as a function of slope change, sensor noise, and distance traveled. In one implementation of this embodiment, the grid size of a map is constant. In addition, in some embodiments, the terrain correlation is used to offset for changes in the step length associated with an identified gait of the user when going up or down a slope.

In addition, the system 100, in this example, incorporates the information gathered from the GPS sensor 38 or other radio frequency positioning aids to obtain accurate geographic location and distance traveled information. GPS provides superior position and distance traveled information as compared to conventional inertial navigation systems. The personal navigation system 100 uses the GPS sensor 38 to acquire an initial position estimate. The Kalman filter functionality 108 is configured to use data input from the GPS sensor 38 in addition to the distance-traveled estimates from the wavelet motion classification functionality 106 to calculate updates to the navigation solution. However, GPS, and other RF location aids, are not always available because of satellite or transmitter outages, obstacles to radio-signal transmission, and so forth. In some such cases, the personal navigation system 100 relies on the wavelet motion classification functionality 106 to estimate the individual's distance traveled as an aid to the inertial navigation processing block via the Kalman filter.

Although the system described above is a personal navigation system used to calculate a navigation solution, the wavelet motion classification functionality 106 can be implemented in other systems. For example, in other embodiments, the wavelet motion classification functionality 106 is implemented in a health and behavior monitoring system. In particular, within the medical field it is important to understand and develop models for how people move. Such models can benefit a wide variety of tasks such as detection and monitoring of physical disorders, as well as evaluating early childhood locomotion. For example, by quantifying each child's motion over time using a system such as system 100, it can be determined how much time each child in a group of children spends in different crawling modes, as well as walking modes. Such data could be used to increase our understanding of early childhood development, allowing researchers to study factors which impact physical development and/or physical disorders.

Figure 5:
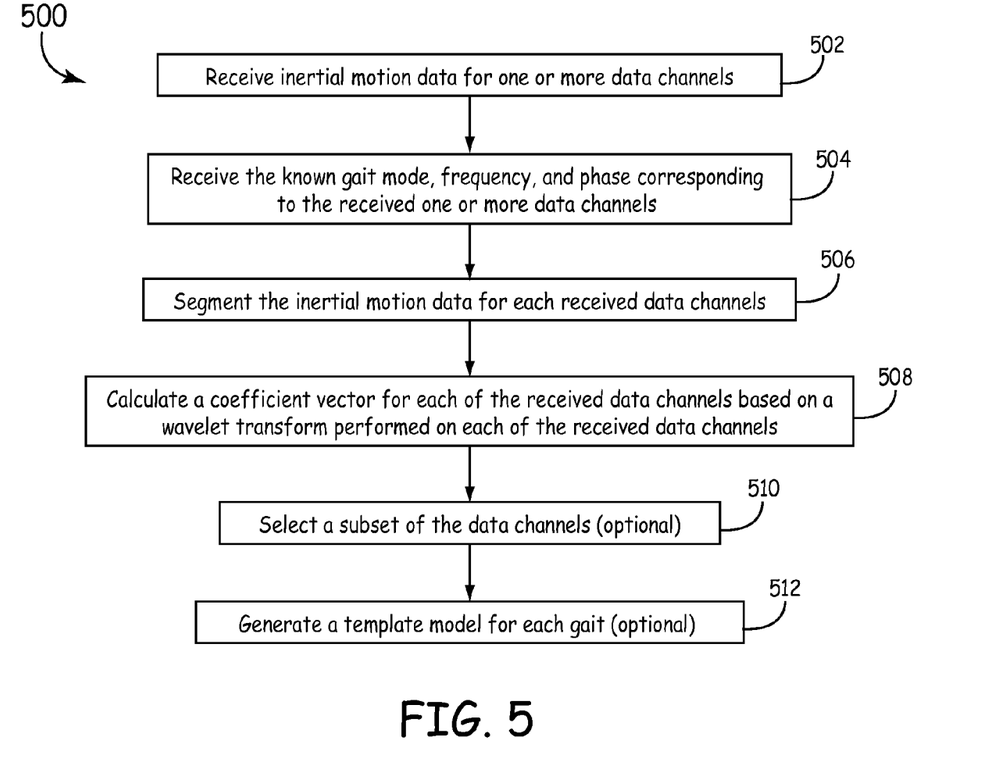
FIG. 5 is a flow chart of one embodiment of a method of generating templates for motion classification.

FIG. 5 is a block diagram of the training phase method 500, which is employed for generating templates for motion classification. Method 500 can be implemented by wavelet motion classification functionality 106 described above. At block 502, inertial motion data for one or more data channels is received as described above. In particular, in this embodiment, data from six channels is received. At block 504, the known gait mode, frequency and phase corresponding to the inertial motion data is received. At block 506, the inertial motion data for each received data channels is segmented. That is, cycles of the repetitive motions or steps are identified and separated. In some embodiments, segmenting the data includes calculating an average step computed from the individual steps that are segmented as discussed above.

At block 508, a wavelet transformation is performed on each of the received data channels, as described above, to calculate a coefficient vector. In some embodiments, the coefficient vector for each channel is correlated with the known gait, frequency, and phase and saved as a gait template. For example, in some embodiments, data is collected from each channel for each of a plurality of users. Each user is monitored while moving using each of the different gait modes to obtain ground truth. In addition, each user repeats each gait mode at different frequencies, and the collected data is shifted to obtain examples at different phases. Thus, in some embodiments, a template is stored corresponding to gait mode, frequency, and phase for each channel of data from each user.

When data for a plurality of channels is received at block 502, a subset of the plurality of channels is optionally selected at block 510. In other words, rather than using the data from all of the plurality of channels, a smaller subset of the plurality of channels is selected. By using a subset containing less than the total number of channels, processing of the data can be sped up to reduce the time and system requirements needed to generate the corresponding templates. In particular, rather than storing or using the coefficient vectors for each gait mode, frequency and phase for each channel, only the coefficient vectors for the selected subset of channels are used and/or stored. Selecting the subset of channels is also referred to herein as "feature selection". As used herein, the term "feature" refers to a channel of data from the IMU 102.

For example, in this embodiment, a forward feature selection method is used to select the subset of channels. The forward feature selection starts with the simplest model using just one feature (e.g., one channel among the six channels), and then sequentially adds more features one at a time. The addition of another feature is accepted only if the addition produces a model that results in a statistically significant decrease in the value of the loss function.

The loss function is defined for two scenarios in this embodiment. The first scenario is defined by the motion class classification and the frequency estimation. The second scenario is defined by the motion class classification and the phase estimation. The major component in the loss function is for the motion classification. That is, if the motion classification result for a test data is wrong, then the loss function for that test data is 1 and the frequency estimation and phase estimation are not needed or calculated. However, if the motion classification result for a test data is correct, then frequency loss or phase loss is added, in some embodiments, to see the model's performance in more detail.

For the first scenario, if the motion class estimated from a given feature is equal to the actual motion class, then the frequency loss function, $L_f$, is defined by the following equation:

$L_f = L_f(f_{est}, f_{true})$, where $f_{est}$ is the estimated frequency and $f_{true}$ is the true or actual frequency. For example, the loss function $L_f$ can be the L1-norm or L2-norm of the difference between $f_{est}$ and $f_{true}$.

If the motion class estimated from a given feature is not equal to the actual motion class, then the frequency loss function, $L_f$, is assigned the value '1'.

Similarly, for the second scenario, if the motion class estimated from a given feature is equal to the actual motion class, then the phase loss function, $L_p$, the following equation:

$L_p = L_p(P_{est} - P_{true})$, where $P_{est}$ is the estimated phase and $P_{true}$ is the true or actual phase.

If the motion class estimated from the given feature is not equal to the actual motion class, then the phase loss function, $L_p$, is assigned the value '1'. In both scenarios, the estimated frequency and phase are determined by analyzing the segmented steps. The ground truth (i.e. labeled data) for the gait mode, frequency, and phase of each example step can be obtained using various techniques. For example, in one embodiment, expert knowledge of an experiment moderator can be used to label the portions of data which correspond to each gait. In other embodiments, the ground truth for the frequency is obtained by computing the frequency domain (e.g., via fast Fourier transform) of the input signal and determine the dominant step frequency. In some embodiments, the ground truth for the phase is obtained by manually selecting a starting signal location for each gait mode and manually fixing this location to be the "zero-phase" location.

When in the training mode, the actual motion class (gait mode), frequency, and phase are known. Thus, the estimated motion class, phase, and frequency can be compared to the actual motion class, frequency, and phase to calculate values for the loss functions. Exemplary values of the frequency and phase loss functions are shown in Table 1(a) below. In Table 1(a), w_x, w_y and w_z represent the channel corresponding to the three gyros measuring angular motion about the x, y, and z axes, respectively. In Table 1(a) a_x, a_y, and a_z represent the channel corresponding to the three accelerometers measuring linear motion along the x, y, and z axes, respectively.

TABLE 1(a)

|  | Loss function using motion class classification and frequency estimation | Loss function using motion class classification and phase estimation |
| --- | --- | --- |
| w_x | 0.6728 | 0.6654 |
| w_y | 0.1626 | 0.1269 |
| w_z | 0.2723 | 0.2346 |
| a_x | 0.2740 | 0.2308 |
| a_y | 0.0949 | 0.0500 |
| a_z | 0.0592 | 0.0808 |

In the exemplary data for a duck walk gait in Table 1(a), the a_z channel has the smallest loss function values using the 'motion class and frequency loss function', and the a_y channel has the smallest loss function value using 'motion class and phase loss function'. In this example, the a_z channel is first selected as the simplest model. Exemplary values of the loss functions resulting from the combination of the a_z channel data with the other channels are shown in Table 1(b).

TABLE 1(b)

|  | Loss function using motion class classification and frequency estimation | Loss function using motion class classification and phase estimation |
| --- | --- | --- |
| a_z + w_x | 0.4203 | 0.4346 |
| a_z + w_y | 0.1269 | 0.0846 |
| a_z + w_z | 0.1645 | 0.1192 |
| a_z + a_x | 0.0908 | 0.0385 |
| a_z + a_y | 0.0592 | 0.0115 |

As shown in Table 1(b) the combination of the a_z and a_y channels results in the smallest loss function. To determine if the addition of another channel results in a statistically significant difference, the F-test, known to one of skill in the art, is used. The F-test has an F-distribution of loss function values under the null hypothesis. The null hypothesis is that the additional channel will not result in a statistically significant difference. The null hypothesis is rejected if the value of F calculated from the combined data is greater than the critical value of the F distribution for some desired false-rejection probability. For example, the critical value can be set to correspond to a 5% significance level.

The F-distribution is a family of continuous distributions indexed by two parameters known as the degrees of freedom. The degrees of freedom are defined as $m_1$ for the first model, and $m_2$ for the second model, and n is the total number of samples for all the channels. For example, in determining if the combination of a_z and a_y provides a statistically significant reduction in the loss function, the value of $m_1$ is the degree of freedom for using the a_z channel, and $m_2$ is the degree of freedom for using the combined a_z and a_y channels. The equation for determining the F value is defined as:

$$F = \frac{\left(\frac{L_2 - L_1}{m_2 - m_1}\right)}{\left(\frac{L_2}{n - m_2}\right)}$$

In the above equation, $L_1$ is the loss function of the first model, $L_2$ is the loss function of the second model. For example, the first model can be from using one channel of IMU data. The second model can be obtained from using two channels of IMU data representing, for example, the values of the loss functions for the combination of the two channels.

Therefore, the null hypothesis that the additional channel will not result in a significant reduction in the loss function is rejected if the calculated F value is greater than the critical value. When the null hypothesis is rejected, the additional channel is included. The addition of channels continues until the calculation of the F value does not result in a value that exceeds the critical value. By performing this analysis for each gait mode based on the training data, the relevant channels for each gait mode can be selected. For example, for the duck walking gait mode in this exemplary implementation, the results of selected subsets of channels are channel a_z, channel a_y, and channel a_x.

It is to be understood that the values in Tables 1(a) and 1(b) are provided by way of example and that the values may vary depending on the inertial motion data gathered. In addition, although the F-test is used in this example to select a subset of channels, it is to be understood that other statistical tests can be used in other embodiments to select a subset of channels.

At block 512, a template model for each gait is optionally generated. The template model captures the distribution of templates for a given gait. In other words, a single template model is used for each gait rather than having a plurality of templates for each user, frequency and mode associated with a given gait. In this embodiment, a one class Support Vector Machine (SVM) with Radial Basis Function (RBF) as the kernel is used to capture the distribution of templates for different users into a single template model for each gait.

The calculation of each gait template model only uses the training data belonging to the particular gait. For example, the walking gait template model only uses the walking data to build the walking gait template model. Thus, the one class SVM with RBF captures the distribution of the training data for a particular gait. The one class SVM can use all the channels of the IMU data. Also when the feature selection at block 510 is used, the one class SVM only uses the data from the selected subclass of channels to capture the distribution of training data for a particular gait.

Given finite data samples ($x_i$, i=1, ..., n), the one class SVM finds a region in the input space where the data predominantly lies or the unknown probability density is relatively large (e.g. exceeds some threshold). This is referred to as single class learning because all training samples are from one class. The radial basis function maps the input space to a high dimensional space, where the possible parameterization of f (x, ω) is a hypersphere whose boundary is defined by its radius r and center a. This can be expressed using the following equation:

$$f(x,\omega) = \|x - a\| - r;$$

where x is the input data.

The use of radial basis functions as the kernel is known to one of skill in the art and is not described in more detail herein. The result of solving the above one class SVM equation is a model which captures the distributions of different coefficient vectors for different users for a given gait. After calculating the gait template model, unknown input data can be compared to the gait template model rather than the plurality of templates for each distribution. This further reduces processing requirements when identifying unknown gait modes. In addition, this saves memory when loading the template models during the identification phase as opposed to loading the different gait templates.

Figure 6:
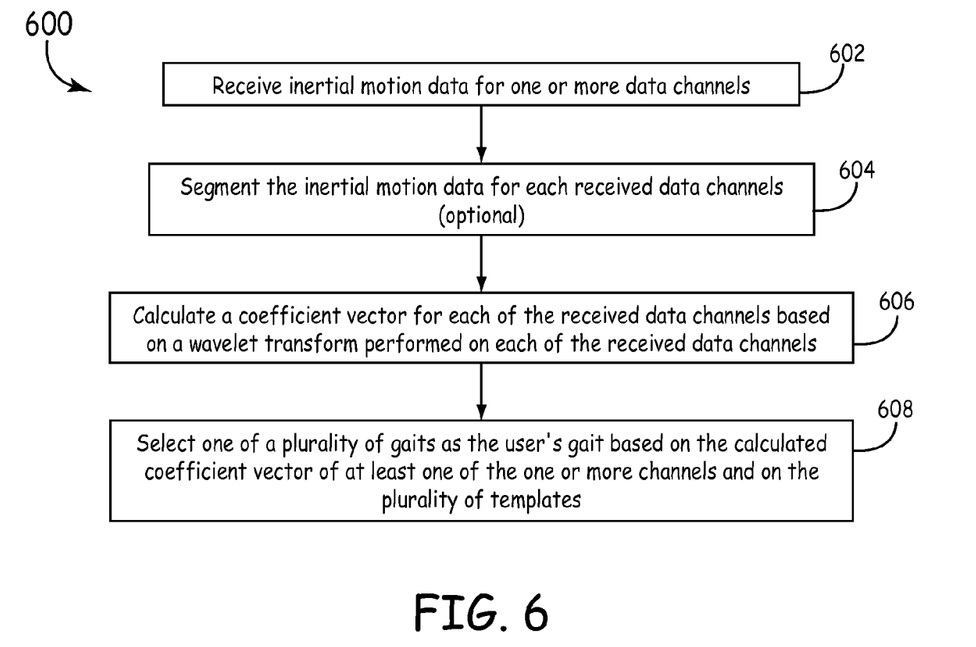
FIG. 6 is a flow chart of one embodiment of a method of identifying a user's gait.

FIG. 6 is a flow chart depicting an exemplary identification phase method 600, which is used to identify a user's gait. Method 600 can be implemented by wavelet motion classification functionality 106 described above. At block 602, inertial motion data from one or more data channels is received as described above. At block 604, the inertial motion data for each of the received data channels is optionally segmented. That is, cycles of the repetitive motion or step are identified and separated. Segmentation of the inertial motion data in the identification phase method 600 can be used to obtain an additional cue that verifies the classified frequency. However, it is to be understood that the inertial motion data is not segmented in every embodiment of the identification method 600.

At block 606, a wavelet transform is performed on the data as described above to calculate a coefficient vector for the received channels. At block 608, one of a plurality of gaits is selected as the user's gait based on the calculated coefficient vector of at least one of the one or more channels and on the plurality of templates, each template corresponding to one of the plurality of gaits. For example, in some embodiments the coefficient vectors are compared to a plurality of templates to identify the gait mode. In some such embodiments, the coefficient vectors for each of the received channels is compared to a plurality of corresponding coefficient vectors for each gait mode to identify the closest match. In other embodiments, a selected subset of channels is compared to the plurality of corresponding coefficient vectors.

For example, when feature selection is performed during the training phase, the subset of channels for each type of gait is identified. Thus, each subset of channels is compared to the templates for the corresponding gait. For example, if the a_y channel is selected as the subset for the walking gait, only the coefficient vector from the a_y channel is compared to the templates for the walking gait. However, if the a_y and w_z channels are selected as the subset for the running gait, then the coefficient vectors from the a_y and w_z channels are compared to the templates for the running gait.

Additionally, when a template model is generated for each gait, such with a one class SVM as described above, then the selected gait is selected based on fitting the coefficient vectors to one template model for each gait. Each template model describes a distribution of the gait templates corresponding to the respective gait. The template model to which the coefficient vector best fits is selected as the user's gait mode. After identifying the gait mode, a distance-traveled estimate can be calculated, as described above, based on the identified gait.

In addition, in order to validate a match of the current query wavelet to a gait template, additional statistical tests to decrease the probability of false positives and negatives can be employed in some embodiments. For example, a threshold can be used which discards all matches which are less than a certain probability level. In effect, after comparing the query wavelet (e.g. using the corresponding coefficient vector) to all of the templates, if the highest matching score is not greater than the threshold, at block 608 the query wavelet is assigned to the "no-model" hypothesis, which means that the person is executing an unknown gait and no step-length update is fed to the Kalman Filter functionality 108.

In another example, the statistical test used to improve the accuracy of the classification method 600 is to compute the ratio between the best matching hypothesis score and the second best hypothesis score. If this ratio is not higher than a threshold, then there are two or more probable gaits. In some such embodiments, when there are two or more probable gaits, it is determined that it is not safe to assign a gait class and the query wavelet is assigned to the no-model hypothesis.

Another exemplary technique employed at block 608 is a sliding window consensus metric. In other words, not only the current classification decision is examined, but also the previous decisions over a time horizon (e.g., the last ten decisions). If a majority of the queries agree on a single gait, then the classification scheme matches the current query wavelet to that gait mode. However, in some embodiments, if there is incongruence in the classification decisions over the time horizon, then the current wavelet query is assigned to the no-model hypothesis. It is to be understood that the exemplary statistical techniques described above are provided by way of example and that other techniques can be used in other embodiments to validate a match of the current query wavelet to a gait template.

Although specific embodiments have been illustrated and described herein, it will be appreciated by those of ordinary skill in the art that any arrangement, which is calculated to achieve the same purpose, may be substituted for the specific embodiments shown. Therefore, it is manifestly intended that this invention be limited only by the claims and the equivalents thereof.

What is claimed is:

1. A motion classification system comprising:
an inertial measurement unit configured to sense motion of a user and to output a plurality of channels of inertial motion data corresponding to the sensed motion; and
a processing unit configured to calculate a coefficient vector for each of the plurality of channels based on a wavelet transformation of the respective inertial motion data, and to select one of a plurality of gaits as the user's gait based on the calculated coefficient vector of at least one of the plurality of channels and on a plurality of templates, each template corresponding to one of the plurality of gaits;
wherein each template is associated with a respective subset of the plurality of channels based on the respective gait to which each template corresponds;
wherein the processing unit is configured to compare each template to the coefficient vector of each channel in the respective subset of the plurality of channels.

2. The motion classification system of claim 1, wherein the processing unit is further configured to calculate a distance-traveled estimate based, in part, on the selected gait; wherein the processing unit is configured to update a navigation solution based on the distance-traveled estimate.

3. The motion classification system of claim 2, wherein the motion classification system further comprises:
one or more aiding sensors each configured to sense motion of the user and output signals corresponding to the user's motion;
wherein the processing unit is further configured to update the navigation solution based on the signals from the one or more aiding sensors.

4. The motion classification system of claim 1, wherein, during a training phase, the inertial measurement unit is configured to output a plurality of channels of inertial motion data; and
wherein, during the training phase, the processing unit is configured to receive user input indicating actual user gait corresponding to the inertial motion data from the plurality of channels; to segment the inertial motion data from each of the plurality of channels, and to calculate a coefficient vector for each of the plurality of channels based on a wavelet transformation of the respective segmented inertial motion data;
wherein the processing unit is further configured to correlate the coefficient vector for each of the plurality of channels with the user input indicating actual user gait to generate the plurality of templates.

5. The motion classification system of claim 4, wherein, during the training phase, the processing unit is configured to correlate the coefficient vector for each channel in a subset of the plurality of channels with the user input indicating actual user gait to generate the plurality of templates.

6. The motion classification system of claim 5, wherein, during an identification phase, the inertial measurement unit is configured to output a plurality of channels of inertial motion data; and
wherein, during the identification phase, the processing unit is configured to select one of the plurality of gaits as the user's gait based on the coefficient vector for each channel of a subset of the plurality of channels.

7. The motion classification system of claim 4, wherein, during the training phase, the processing unit is configured to generate a single template model for each of the plurality of gaits, each template model describing a distribution of coefficient vectors corresponding to the respective gait.

8. The motion classification system of claim 7, wherein, during an identification phase, the processing unit is configured to select one of the plurality of gaits as the user's gait based on fitting the coefficient vector for at least one of the one or more channels to the respective template model of the selected gait.

9. A method of classifying a user's gait, the method comprising:
receiving, in a processing unit, inertial motion data from a plurality of data channels;
calculating, in a processing unit, a coefficient vector for each of the plurality of data channels based on a wavelet transform of the respective inertial motion data; and
selecting, in a processing unit, one of a plurality of gaits as the user's gait based on the calculated coefficient vector of at least one of the plurality of data channels and on a plurality of templates, each template corresponding to one of the plurality of gaits;

wherein each template is associated with a respective subset of the plurality of data channels based on the respective gait to which each template corresponds; and wherein selecting one of the plurality of gaits comprises comparing a respective subset of the coefficient vectors to each template, each respective subset of the coefficient vectors corresponding to the respective subset of the plurality of data channels associated with each template.

10. The method of claim 9, further comprising:
generating the plurality of templates, wherein generating the plurality of templates comprises:
  receiving inertial motion data from a plurality of data channels;
  receiving user input data indicating the gait mode corresponding to the inertial motion data from the plurality of data channels;
  segmenting the inertial motion data for each of the plurality of data channels;
  calculating a coefficient vector for each of the plurality of data channels; and
  correlating the coefficient vector for each of the plurality data channels with the user input indicating actual user gait.

11. The method of claim 10, wherein segmenting the inertial motion data for each of the plurality of data channels comprises calculating an average step for each of the plurality of data channels based on the segmented inertial motion data.

12. The method of claim 10, wherein generating the plurality of templates further comprises:
  selecting a subset of the plurality of data channels; and
  wherein correlating the coefficient vector comprises correlating the coefficient vector for each of the data channels in the subset of the plurality of data channels with the user input indicating actual user gait.

13. The method of claim 10, wherein generating the plurality of templates further comprises:
  generating a single template model for each of the plurality of gaits, each template model describing a distribution of coefficient vectors corresponding to the respective gait.

14. The method of claim 9, further comprising:
  calculating a distance-traveled estimate based on the selected gait; and
  updating a navigation solution based on the distance-traveled estimate.

15. A program product comprising a non-transitory processor-readable medium on which program instructions are embodied, wherein the program instructions are configured, when executed by at least one programmable processor, to cause the at least one programmable processor to:

calculate a coefficient vector for each of a plurality of data channels based on a wavelet transform of respective inertial motion data for each of the plurality of data channels; and select one of a plurality of gaits as the user's gait based on the calculated coefficient vector of at least one of the plurality of data channels and on a plurality of templates, each template corresponding to one of the plurality of gaits;

wherein each template is associated with a respective subset of the plurality of data channels based on the respective gait to which each template corresponds; and wherein the program instructions are further configured to cause the at least one programmable processor to compare each template to a respective subset of the coefficient vectors, each respective subset of the coefficient vectors corresponding to the respective subset of the plurality of data channels associated with each template.

16. The program product of claim 15, wherein the program instructions are further configured to cause the at least one programmable processor to generate the plurality of templates by:
  segmenting the inertial motion data for each of a plurality of data channels;
  calculating a coefficient vector for each of the plurality of data channels; and
  correlating the coefficient vector for each of the plurality data channels with user input indicating actual user gait.

17. The program product of claim 16, wherein the program instructions are further configured to cause the at least one programmable processor to calculate an average step for each of the plurality of data channels based on the respective segmented inertial motion data.

18. The program product of claim 16, wherein the program instructions are further configured to cause the at least one programmable processor to generate the plurality of templates by:
  selecting a subset of the plurality of data channels; and
  correlating the coefficient vector for each of the data channels in the subset of the plurality of data channels with the user input indicating actual user gait.

19. The program product of claim 16, wherein the program instructions are further configured to cause the at least one programmable processor to generate the plurality of templates by generating a single template model for each of the plurality of gaits, each template model describing a distribution of coefficient vectors corresponding to the respective gait.

20. The program product of claim 19, wherein the program instructions are further configured to cause the at least one programmable processor to select one of the plurality of gaits as the user's gait by fitting the coefficient vector for the at least one of the one or more data channels to the respective template model of the selected gait.

* * * * *